(12) United States Patent
Okamoto et al.

(10) Patent No.: US 9,181,153 B2
(45) Date of Patent: Nov. 10, 2015

(54) METHOD FOR PRODUCING (E)-1-CHLORO-3,3,3-TRIFLUOROPROPENE

(71) Applicant: Central Glass Company, Limited, Ube-shi, Yamaguchi (JP)

(72) Inventors: Masamune Okamoto, Fujimino (JP); Hideaki Imura, Saitama (JP); Naoto Takada, Saitama (JP); Tatsuya Hayasaka, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/353,608

(22) PCT Filed: Oct. 3, 2012

(86) PCT No.: PCT/JP2012/075605
§ 371 (c)(1),
(2) Date: Apr. 23, 2014

(87) PCT Pub. No.: WO2013/069390
PCT Pub. Date: May 16, 2013

(65) Prior Publication Data
US 2015/0011805 A1    Jan. 8, 2015

(30) Foreign Application Priority Data

Nov. 11, 2011  (JP) .................................. 2011-247125

(51) Int. Cl.
| | | |
|---|---|---|
| *C07C 17/00* | (2006.01) | |
| *C07C 17/23* | (2006.01) | |
| *C07C 17/383* | (2006.01) | |
| *C07C 17/395* | (2006.01) | |

(52) U.S. Cl.
CPC .............. *C07C 17/23* (2013.01); *C07C 17/383* (2013.01); *C07C 17/395* (2013.01); *C07B 2200/09* (2013.01)

(58) Field of Classification Search
CPC ...... C07C 17/383; C07C 17/395; C07C 21/18
USPC ........................................................ 570/155
See application file for complete search history.

(56) References Cited

U.S. PATENT DOCUMENTS

| | | | |
|---|---|---|---|
| 6,013,846 A | 1/2000 | Wismer et al. | |
| 6,018,084 A | 1/2000 | Nakada et al. | |
| 6,235,951 B1 | 5/2001 | Sakyu et al. | |
| 6,329,559 B1 | 12/2001 | Sievert et al. | |
| 6,472,573 B1 | 10/2002 | Yamamoto et al. | |
| 6,844,475 B1 | 1/2005 | Tung et al. | |
| 2005/0033097 A1 | 2/2005 | Tung et al. | |
| 2010/0152504 A1 | 6/2010 | Hulse et al. | |
| 2011/0172472 A1* | 7/2011 | Sakyu et al. | ................... 570/160 |
| 2012/0010449 A1 | 1/2012 | Wismer et al. | |

FOREIGN PATENT DOCUMENTS

| | | |
|---|---|---|
| CN | 1224707 A | 8/1999 |
| CN | 1228403 A | 9/1999 |
| CN | 100445247 C | 12/2008 |
| JP | 9-194404 A | 7/1997 |
| JP | 10-67693 A | 3/1998 |
| JP | 11-269105 A | 10/1999 |
| JP | 2001-181220 A | 7/2001 |
| JP | 2002-516888 A | 6/2002 |
| JP | 2007-501843 A | 2/2007 |
| WO | WO 97/24307 A1 | 7/1997 |
| WO | WO 2010/111067 A1 | 9/2010 |

OTHER PUBLICATIONS

International Search Report (PCT/ISA/210) with English translation dated Jan. 8, 2013 (5 pages).
Japanese-language Written Opinion (PCT/ISA/237) dated Jan. 8, 2013 (3 pages).
Chinese Office Action dated Nov. 3, 2014 (Six (6) pages).

* cited by examiner

*Primary Examiner* — Jafar Parsa
(74) *Attorney, Agent, or Firm* — Crowell & Moring LLP

(57) ABSTRACT

The present invention provides a process for purifying a (E)-1-chloro-3,3,3-trifluoropropene composition (OF-1233E composition) in which at hydrogen fluoride and 2-chloro-1,1,1,3,3-pentafluoropropane are contained by bringing the (E)-1-chloro-3,3,3-trifluoropropene composition into contact with a weak base and a method for producing (E)-1-chloro-3,3,3-trifluoropropene composition by distilling the (E)-1-chloro-3,3,3-trifluoropropene composition obtained by such a purification process. This makes it possible to efficiently produce OF-1233E by removing the hydrogen fluoride from the OF-1233E composition, without generating any new component difficult to separate by distillation, and subjecting the resulting composition to distillation.

8 Claims, No Drawings

METHOD FOR PRODUCING (E)-1-CHLORO-3,3,3-TRIFLUOROPROPENE

FIELD OF THE INVENTION

The present invention relates to a process for removing hydrogen fluoride from a composition of (E)-1-chloro-3,3,3-trifluoropropene (trans-1-chloro-3,3,3-trifluoropropene; also referred to as "OF-1233E") and to a method for producing (E)-1-chloro-3,3,3-trifluoropropene using such a process.

BACKGROUND ART

OF-1233E is useful as cleaning agents, refrigerants, heat mediums for heat pumps, high-temperature working fluids etc. It is known that OF-1233E is obtained as a component in a reaction product by fluorination of 1,1,1,3,3-pentachloropropane (HCC-240fa) with hydrogen fluoride (see Patent Document 1). Herein, the reaction product also contains organic substances such as an isomer, i.e., cis-1-chloro-3,3,3-trifluoropropene (also referred to as "OF-1233Z") and by-products or intermediates, e.g., 3-chloro-1,1,1,3-tetrafluoropropane (also referred to as "HCFC-244fa"), 2-chloro-1,1,1,3,3-pentafluoropropane (also referred to as "HCFC-235da") etc., hydrogen chloride and unreacted hydrogen fluoride.

There are disclosed techniques for removing the hydrogen chloride or hydrogen fluoride from the reaction product by washing the reaction product with water (Patent Document 1) or aqueous potassium hydroxide solution (Patent Document 2).

PRIOR ART DOCUMENTS

Patent Documents

Patent Document 1: Japanese Laid-Open Patent Publication No. H11-269105
Patent Document 2: Japanese Laid-Open Patent Publication (Translation of PCT Application) No. 2007-501843

SUMMARY OF THE INVENTION

Problems to be Solved by the Invention

In general, distillation is a simple technique for purifying OF-1233E from the reaction product (OF-1233E composition). However, the unreacted hydrogen fluoride remaining in the OF-1233E composition could be a cause of damage to distillation equipment. It is thus common practice to remove, in advance, the unreacted hydrogen fluoride by adsorption onto solid adsorbent such as sodium fluoride or by washing with water or aqueous base solution.

In the removal of the hydrogen fluoride by adsorption onto sodium fluoride, the regeneration or disposal of the hydrogen fluoride after the use becomes difficult with increase in treatment amount. The removal of the hydrogen fluoride by washing with water is easy in operation. In the removal of the hydrogen fluoride by washing with water, however, there is a possibility of causing equipment corrosion. Further, the removal of the hydrogen fluoride by washing with water is inefficient as it is necessary to repeat operation because of low washing efficiency. In the removal of the hydrogen fluoride by washing with aqueous base solution as disclosed in Patent Document 2 etc., a new, difficult-to-distill component may be generated due to the use of e.g. potassium hydroxide as the base.

It is accordingly an object of the present invention to provide a process for removing, from a OF-1233E composition containing hydrogen fluoride, the hydrogen fluoride without generating any new difficult-to-distill component and to provide a method for efficient production of OF-1233E.

Means for Solving the Problems

When a OF-1233E composition is washed with the use of e.g. sodium hydroxide, new components may be generated by decomposition of OF-1233E, HCFC-244fa, HCFC-235da etc. in the OF-1233E composition. Among others, a compound of formula: $C_3HClF_4$ (also referred to as "OF-1224") generated by dehydrofluorination of HCFC-235da closely resembles OF-1233E in distillation behavior. It is very difficult to separate such a compound by distillation.

Hence, extensive researches have been made on various kinds of bases used for washing of the OF-1233E composition. It has consequently been found that, when the OF-1233E composition is washed with the use of a specific kind of organic base or inorganic base, there is not generated OF-1224 so that the thus-obtained OF-1233E composition contains organic substances separatable by ordinary distillation purification but does not contain hydrogen fluoride. The present invention is based on such a finding.

Namely, the present invention includes the following aspects.

[Inventive Aspect 1]
A purification process of a (E)-1-chloro-3,3,3-trifluoropropene composition, the (E)-1-chloro-3,3,3-trifluoropropene composition containing at least hydrogen fluoride and 2-chloro-1,1,1,3,3-pentafluoropropane, the purification method comprising: bringing the (E)-1-chloro-3,3,3-trifluoropropene composition into contact with a weak base.

[Inventive Aspect 2]
The purification process of the (E)-1-chloro-3,3,3-trifluoropropene composition according to Inventive Aspect 1, wherein the weak base has a pKa of 7 to 11.

[Inventive Aspect 3]
The purification process of the (E)-1-chloro-3,3,3-trifluoropropene composition according to Inventive Aspect 1, wherein the weak base is selected from the group consisting of carbonates, hydrocarbonates, phosphates, hydrogenphosphates, dihydrogenphosphates and $C_1$-$C_6$ carboxylates of alkali metals and $C_3$-$C_{15}$ tertiary amines.

[Inventive Aspect 4]
The purification process of the (E)-1-chloro-3,3,3-trifluoropropene composition according to Inventive Aspect 1, wherein the weak base is selected from the group consisting of hydrocarbonate of sodium or potassium, carbonate of sodium or potassium, acetate of sodium or potassium and triethylamine.

[Inventive Aspect 5]
A production method of (E)-1-chloro-3,3,3-tifluoropropene, comprising: distilling a (E)-1-chloro-3,3,3-trifluoropropene composition obtained by the purification process according to any one of Inventive Aspects 1 to 4.

In the present invention, the hydrogen fluoride is efficiently removed from the OF-1233E composition by contact of the OF-1233E composition with the weak base. In such a purification process, there is not generated OF-1224 that closely resembles OF-1233E in distillation behavior. It is thus possible to purify OF-1233E from the OF-1233E composition by simple distillation. The adoption of such a purification process enables easy production of high-purity OF-1233E.

DESCRIPTION OF THE EMBODIMENTS

The purification process according to the present invention includes contact treatment of the OF-1233E composition containing HCFC-235da with the weak base as mentioned above.

In the present invention, the OF-1233E composition containing HCFC-235da can be obtained by any process and used for contact treatment with the weak base. The OF-1233 composition may be a reaction product obtained by reaction of 1,1,1,3,3-pentachloropropane (HCC-240fa) with hydrogen fluoride or may be a composition obtained by known purification treatment of such a reaction product. As the purification treatment, there can be adopted washing with water or liquid, drying, selective adsorption onto solid adsorbent, ordinary distillation, extraction distillation etc. The OF-1233 composition may be in the form of a mixture for uses as solvents, cleaning agents, refrigerants, heat mediums etc.

For example, it is feasible to obtain OF-1233E together with OF-1233Z by reaction of 1,1,1,3,3-pentafluoropropane (HCC-240fa) with hydrogen fluoride in a gas phase in the presence of a catalyst such as alumina or fluorinated alumina. The resulting reaction product contains OF-1233E and various fluorinated hydrocarbons (each of which may contain a hydrogen atom and may contain any halogen atom other than fluorine) as organic components. In general, HCFC-235fa is contained in an amount of 5 mass % or less. The reaction product contains acid components such as hydrogen chloride and hydrogen fluoride in addition to the organic substances. The hydrogen fluoride removal process according to the present invention can be applied to such a crude fluorination reaction product or OF-1233 composition obtained by preliminary purification treatment of the crude fluorination reaction product. The OF-1233 composition may be again treated by the process according to the present invention.

Examples of the OF-1233E composition obtained by the preliminary purification treatment are those obtained by distilling the organic components and the hydrogen chloride, which has a large difference in boiling point relative to the hydrogen fluoride, out from the crude reaction product, by removing the hydrogen chloride from the crude reaction product upon contact with at least water (in this case, a given amount of the hydrogen fluoride remains in the composition even though some of the hydrogen fluoride is removed by water washing), and by distilling the OF-1233E composition containing at least hydrogen fluoride and thereby changing the content ratio of the organic components in the composition.

When the OF-1233E composition is brought into contact with the weak base after the preliminary purification treatment, the amount of the hydrogen fluoride contained in the OF-1233E composition is generally 0.0001 to 10 parts by mass, preferably 0.001 to 5 parts by mass, more preferably 0.01 to 2 parts by mass, per 100 parts by mass of the OF-1233E composition. If the amount of the hydrogen fluoride contained in the OF-1233E composition is less than 0.0001 parts by mass, there is less necessity to bring the OF-1233E composition with the weak base according to the present invention. The OF-1233E composition can be treated by contact with the weak base according to the present invention even if the amount of the hydrogen fluoride contained in the OF-1233E composition exceeds 10 parts by mass. It is however efficient to reduce in advance the amount of the hydrogen fluoride contained in the OF-1233E composition by the preliminary purification treatment etc. and is thus preferable to avoid such a high hydrogen fluoride content.

The weak base can be any known inorganic or organic weak base. In general, it is preferable that the weak base has a pKa of 7 to 11. Examples of the inorganic weak base are carbonates, hydrogencarbonates, phosphates, hydrogenphosphates and dihydrogenphosphates of alkali metals. Examples of the organic weak base are $C_1$-$C_6$ carbonates of alkali metals and $C_3$-$C_{15}$ tertiary amines.

The alkali metals are lithium, sodium, potassium, rubidium and cesium. Among others, lithium, sodium or potassium is preferred. More preferred is sodium or potassium.

Specific examples of the alkali metal salts usable as the weak base are lithium carbonate, lithium hydrogencarbonate, lithium phosphate, lithium hydrogenphosphate, lithium dihydrogenphosphate, sodium carbonate, sodium hydrogencarbonate, sodium phosphate, sodium hydrogenphosphate, sodium dihydrogenphosphate, potassium carbonate, potassium hydrogencarbonate, potassium phosphate, potassium hydrogencarbonate and potassium dihydrogencarbonate.

The $C_1$-$C_6$ carboxylates are salts of $C_1$-$C_6$ carboxylic acids such as formic acid, acetic acid, propionic acid, butyric acid and valeric acid. Among others, formic acid or acetic acid is preferred as the $C_1$-$C_6$ carboxylic acid. Specific examples of the carboxylates are lithium acetate, sodium formate, sodium acetate, potassium formate and potassium acetate.

Examples of the $C_3$-$C_{15}$ tertiary amine are: linear amines such as symmetric tertiary amines typified by trimethylamine, triethylamine, tri-n-propylamine, tri-isopropylamine, tri-n-butylamine, tri-isobutylamine, tri-sec-butylamine, tri-tert-butylamine, tri-n-amylamine, tri-isoamylamine, tri-sec-amylamine, tri-tert-amylamine, N,N,N',N'-tetramethylethylenediamine, N,N,N',N'-tetramethylpropane-1,3-diamine and tetramethylguanidine and asymmetric tertiary amines typified by N-methyldiethylamine, N-methyldi-n-propylamine, N-methyldiisopropylamine, N-methyldi-n-butylamine, N-methyldiisobutylamine, N-methyldi-tert-butylamine, N,N-diisopropylbutylamine, N,N-dimethyl-n-octylamine, N,N-dimethylnonylamine, N,N-dimethyldecylamine, N,N-dimethylundecylamine, N,N-dimethyldodecylamine and N-methyldihexylamine; and cyclic amines typified by N,N'-dimethylpiperazine, 1,8-diazabicyclo[5.4.0]-7-undecene (DBU), 1,4-diazabicyclo[2.2.2]octane (DABCO) and bis(2-dimethylaminoethyl)ether.

As the weak base, particularly preferred is hydrogencarbonate of sodium or potassium, carbonate of sodium or potassium, acetate of sodium or potassium or triethylamine.

The amount of the weak base used is generally 1 to 10 mol, preferably 1 to 5 mol, more preferably 1 to 2 mol, in terms of monobasic acids per 1 mol of the hydrogen fluoride contained in the OF-1233E composition. If the amount of the weak base used is less than 1 mol, the weak base is stoichiometrically insufficient. It is thus unfavorable to use the weak base in such a small amount. It is waste to use the weak base in an amount exceeding 10 mol. Further, the disposal of the treatment solution becomes difficult if the amount of the weak base used exceeds 10 mol.

In the case where the inorganic salt or carbonate is used as the weak base, it is preferable to use the weak base in combination with a solvent such as water or organic solvent. Examples of the organic solvent are water-soluble solvents such as alcohols e.g. methanol and ethanol and ketones e.g. acetone. As the solvent, water is particularly preferred. It suffices that the weak base can be dissolved in the solvent. The concentration of the weak base in the resulting solution is in the range up to the saturated solubility. More specifically, the concentration of the weak base in the solution is generally 0.01 to 50 mass %, preferably 0.1 to 30 mass %, 0.5 to 10 mass %. It is unfavorable that the weak base concentration is less than 0.01 mass % because such a low weak base concentration results in upsizing of treatment equipment. It is also unfavorable that the weak base concentration exceeds 50 mass % because such a high weak base concentration can cause a precipitate of salt (e.g. sodium fluoride) and thereby make treatment operation difficult.

In the case where the tertiary amine is used as the weak base, it is feasible to use the weak base in combination with an solvent such as water or organic solvent but is preferable not to use the weak base in combination with any solvent other than water. Examples of the organic solvent are water-soluble solvents such as alcohols e.g. methanol and ethanol and ketones e.g. acetone.

There is no particular limitation on the process for contact of the OF-1233E composition with the weak base. It is easy and preferable to bring the OF-1233E composition into contact with the weak base by liquid-to-liquid contact process. In the case where the tertiary amine of low boiling point, such as trimethylamine, is used as the weak base, the OF-1233E composition can be brought into contact with the weak base under pressurized conditions or low-temperature conditions. For example, it is feasible to bring the OF-1233E composition into contact with the weak base by charging the OF-1233E composition and the weak base into a reaction (treatment) vessel and stirring the content of the reaction vessel. As the stirring means, there can be adopted a known stirring vane of high stirring efficiency, such as screw stirring vane, a liquid flow stirring device with an external or internal pump, a stirring device having a flow-line mixer or a discharge portion equipped with a sparger etc. It is preferable that the treatment vessel is made of a glass material, stainless steel, fluoro resin, a material with a lining of glass, stainless or fluoro resin, etc.

The temperature of the treatment is generally $-5$ to $+50°$ C., preferably 0 to $+30°$ C. It is unfavorable that the treatment temperature is lower than $-5°$ C. because there may occur freezing of the aqueous treatment solution. It is also unfavorable that the treatment temperature exceeds $+50°$ C. because there arises a need to use a pressure-resistant reaction vessel in view of pressure increase inside the reaction vessel and because any component or components of the OF-1233E composition may be involved in reaction. The pressure of the treatment can be atmospheric pressure. In the case where the equipment is a closed system, it is feasible to perform the treatment under self-pressure conditions when the reaction temperature exceeds 19° C. The treatment pressure is thus generally 0.1 to 5 MPa.

The time of the treatment varies depending on the conditions of the contact treatment, such as the ratio of the OF-1233E composition and the weak base, the stirring efficiency, the treatment temperature and the like. The treatment time is generally 1 minute to 100 hours, preferably 30 minutes to 50 hours.

There is no change in the content ratio of the organic substances in the composition (i.e. the content of the reaction vessel) before and after the treatment. In the case where the inorganic salt or carbonate is used as the weak base in aqueous solution form, the content of the reaction vessel after the treatment is separated into two phases. In this case, the organic phase is extracted by separation from the content of the reaction vessel.

In the case where the tertiary amine is used as the weak base, by contrast, the content of the reaction vessel after the treatment includes not only the components of the OE-1233E composition before the treatment but also a free tertiary amine and a salt of tertiary amine and hydrogen fluoride (referred to as "tertiary amine/hydrogen fluoride salt"). There is no particular limitation on the process for extraction of OE-1233E from the content of the reaction vessel. It is conceivable to extract OE-1233E by distillation from the content of the reaction vessel. Depending on the kind of the tertiary amine, however, the distillation may cause decomposition of the tertiary amine/hydrogen fluoride salt to regeneration the hydrogen fluoride. It is thus feasible to extract OE-1233E e.g. by the following procedure.

The OF-1233E composition containing the tertiary amine/hydrogen fluoride salt is stirred with the addition of water. The resulting organic and aqueous phases are separated and extracted. The free tertiary amine e.g. triethylamine and the tertiary amine/hydrogen fluoride salt are contained in the aqueous phase, whereas the same components of the OE-1233E composition as those before the treatment are contained together with a small amount of tertiary amine e.g. triethylamine in the organic phase.

By the addition of a strong base such as inorganic base to the aqueous phase in which the tertiary amine/hydrogen fluoride salt is contained, it is feasible to isolate and separate the tertiary amine from the aqueous phase. Although there is no particular limitation on the inorganic base, the inorganic base is preferably a hydroxide of an alkali metal. The alkali metal can be either sodium, potassium, lithium etc. Specific examples of the inorganic base are sodium hydroxide, potassium hydroxide and lithium hydroxide. Among others, sodium hydroxide or potassium hydroxide is preferred. Particularly preferred is potassium hydroxide.

The recovered tertiary amine can be used, as it is or after drying or purification by distillation, as the weak base.

The organic phase, even when treated by any process, contains no hydrogen fluoride. It is thus possible to subject the organic phase to ordinary purification process for organic reaction products, such as washing with water, drying or distillation. The washing treatment of the organic phase with the weak base does not cause generation of a component difficult to separate from OF-1233E, such as OF-1224, as is different from the washing treatment of the organic phase with a strong base such as sodium hydroxide. It is thus possible to obtain OF-1233E with high purity by distillation of the organic phase.

The organic phase can be subjected to drying before or after the distillation. It is easy to dry the organic phase with the use of a solid drying agent such as synthetic zeolite, silica gel, anhydrous aluminium chloride or phosphorus pentaoxide. Examples of the synthetic zeolite are those of type 3A, 4A, 5A, 13X etc.

EXAMPLES

The present invention will be described in more detail below by way of the following examples. It is herein noted that, unless otherwise specified, the unit "%" of organic composition analysis values means the area percentage "area %" of respective components in chromatographs as measured by gas chromatography with FID.

[Preliminary Washing]

A crude product of (E)-1-chloro-3,3,3-trifluoropropene (OF-1233E) containing hydrogen fluoride (HF) was subjected to preliminary washing with water. The amount of HF contained in the crude OF-1233E product was determined by titration to be 3.0 mass %. On the other hand, a 500-mL autoclave coated with PFA resin and equipped with a blowing tube, a stirring vane and a thermometer, with a soda-lime tube disposed between the autoclave and the outside air, was charged with 100 g of water. Then, 200 g of the crude OF-1233E product was introduced into the autoclave through the blowing tube under nitrogen pressure while the autoclave was cooled with ice in such a manner that the inside temperature of the autoclave did not exceed 15° C. After the introduction of the crude OF-1233E, the content of the autoclave was stirred for 1 hour. The content of the autoclave was subsequently separated by a PFA reparatory funnel, thereby recovering 180 g of a lower organic phase and 105 g of an upper aqueous phase. It was confirmed by ion chromatographic analysis of the aqueous phase that the aqueous phase contained 5.7 g of HF (corresponding to 95% of HF contained in the crude OF-1233E product). It was also confirmed by a pH test paper that the pH of the aqueous phase was 2. Further, HF was extracted from the organic phase with the addition of water. It was confirmed by ion chromatographic analysis that the amount of HF contained in the organic phase was 0.17 mass %.

It was also confirmed by gas chromatographic analysis of the organic phase that the organic phase contained 98.237% of OF-1233E, 0.0775% of HCFC-235da, 0.6728% of OF-1233Z and 0.0001% of OF-1224 difficult to separate by distillation.

Comparative Example 1

In a 50-mL PFA bottle, 15 g of the organic phase after the preliminary washing treatment was placed. Into this bottle, 10 g of water was added. While cooling the bottle in an ice water bath, the content of the bottle was stirred for 2 hours. After that, the bottle was left still in a refrigerator set to 8° C. for 18 hours and separated into two phases. The pH of the aqueous phase was measured by a pH test paper. Further, HF was extracted from the organic phase with the addition of water. The concentration of fluorine ions in the extract was measured by ion chromatography and converted to HF concentration (the same applied to the following examples and comparative examples). The content amounts of organic substances were analyzed by gas chromatography. The HF removal rate was determined by the following equation.

$$HF \text{ removal rate (\%)} = 100 \times \frac{HF \text{ concentration (mass \%)} \text{ of organic composition after washing}}{HF \text{ concentration (mass \%) of organic composition before washing}}$$

Comparative Example 2

The same experiment as that of Comparative Example 1 was conducted using 10 g of 5 mass % aqueous NaOH solution in place of water.

Comparative Example 3

The same experiment as that of Comparative Example 1 was conducted using 10 g of 0.5 mass % aqueous NaOH solution in place of water.

Example 1

The same experiment as that of Comparative Example 1 was conducted using 10 g of 5 mass % aqueous sodium hydrogencarbonate (NaHCO₃) solution in place of water. The organic phase was analyzed after washing twice with 10 ml of water.

Example 2

The same experiment as that of Comparative Example 1 was conducted using 10 g of 0.5 mass % aqueous sodium hydrogencarbonate (NaHCO₃) solution in place of water.

Example 3

The same experiment as that of Comparative Example 1 was conducted using 10 g of 5 mass % aqueous sodium acetate (CH₃COONa) solution in place of water. The organic phase was analyzed after washing twice with 10 ml of water.

Example 4

In a 50-mL PFA bottle, 15 g of the organic phase after the preliminary washing treatment was placed. Into this bottle, 10 g of triethylamine (Et₃N) was added. While cooling the bottle in an ice water bath, the content of the bottle was stirred for 2 hours. After that, the bottle was left still in a refrigerator set to 8° C. for 18 hours. Then, 10 g of water was added into the bottle. While cooling the bottle in an ice water bath, the content of the bottle was stirred for 0.5 hour and separated into two phases. It was confirmed by a pH test paper that the pH of the aqueous phase was 10. Further, HF was extracted from the organic phase with the addition of water. The concentration of fluorine ions in the extract was measured by ion chromatography and converted to HF concentration. The content amounts of organic substances were analyzed by gas chromatography. It was confirmed that: the organic phase contained, as organic substances other than triethylamine, 0.0001% or less of OF-1224, 98.2639% of OF1233E, 0.0751% of HCFC-235da and 0.6470% of OF-1233Z; and there occurred substantially no by-production of OF-1244 difficult to separate by distillation.

The results of Examples 1 to 4 and Comparative Examples 1 to 3 are shown in TABLE 1.

TABLE 1

| | Washing agent | HF removal rate (%) | Solution (pH) | OF-1224 | OF-1233E | HCFC-235da | OF-1233Z |
|---|---|---|---|---|---|---|---|
| Preliminary washing | water | 95 | 2 | <0.0001 | 98.2730 | 0.0775 | 0.6728 |
| Comparative Example 1 | water | 99 | 4 | <0.0001 | 98.1811 | 0.0734 | 0.6409 |
| Comparative Example 2 | 5 mass % NaOH | >99 | >12 | 0.0194 | 98.2778 | 0.0525 | 0.6566 |
| Comparative Example 3 | 0.5 mass % NaOH | >99 | >12 | 0.0107 | 98.0600 | 0.0584 | 0.6090 |
| Example 1 | saturated NaHCO₃ | >99 | 8 | <0.0001 | 98.2339 | 0.0734 | 0.6371 |
| Example 2 | 1 mass % NaHCO₃ | >99 | 8 | <0.0001 | 98.2349 | 0.0745 | 0.6381 |
| Example 3 | sodium acetate | >99 | 6 | <0.0001 | 98.2379 | 0.0722 | 0.6551 |

TABLE 1-continued

| | Washing agent | HF removal rate (%) | Solution (pH) | OF-1224 | OF-1233E | HCFC-235da | OF-1233Z |
|---|---|---|---|---|---|---|---|
| Example 4 | triethyl amine | >99 | 10 | <0.0001 | 98.2639 | 0.0751 | 0.6470 |

OF-1224: chlorotetrafluoropropene
OF-1233E: (E)-1-chloro-3,3,3-trifluoropropene
HCFC-235da: 2-chloro-1,1,1,3,3-pentafluoropropane
OF-1233Z: (Z)-1-chloro-3,3,3-trifluoropropene
NaOH: sodium hydroxide
NaHCO$_3$: sodium hydrogencarbonate $$\text{HF removal rate (\%)} = 100 \times \frac{\text{HF concentration (mass \%) of organic composition after washing}}{\text{HF concentration (mass \%) of organic composition before washing}}$$

As mentioned above, it was possible in Examples 1 to 4 of the present invention to efficiently and easily remove the hydrogen fluoride from the OF-1233E composition without generating any component difficult to separate by distillation, such as OF-1224.

INDUSTRIAL APPLICABILITY

The high-purity OF-1233E obtained by the production method according to the present invention is useful as cleaning agents, refrigerants, heat mediums for heat pumps, high-temperature working fluids etc.

Although the present invention has been described above with reference to the specific exemplary embodiments, the present invention is not limited to these above-described specific exemplary embodiments. Various modifications and variations of the embodiments described above are possible within the range that does not depart from the scope of the present invention.

The invention claimed is:

1. A production process of (E)-1-chloro-3,3,3-trifluoropropene, comprising:
   (a) providing a (E)-1-chloro-3,3,3-trifluoropropene composition, the (E)-1-chloro-3,3,3-trifluoropropene composition containing at least hydrogen fluoride and 2-chloro-1,1,1,3,3-pentafluoropropane; and
   (b) bringing the (E)-1-chloro-3,3,3-trifluoropropene composition into contact with a weak base,
   wherein the weak base is selected from the group consisting of carbonates, hydrocarbonates, phosphates, hydrogenphosphates, dihydrogenphosphates and $C_1$-$C_6$ carboxylates of alkali metals and $C_3$-$C_{15}$ tertiary amines.

2. The production process of (E)-1-chloro-3,3,3-trifluoropropene according to claim 1, wherein the weak base has a pKa of 7 to 11.

3. The production process of (E)-1-chloro-3,3,3-trifluoropropene according to claim 1, wherein the weak base is selected from the group consisting of hydrocarbonate of sodium or potassium, carbonate of sodium or potassium, acetate of sodium or potassium and triethylamine.

4. The production process of (E)-1-chloro-3,3,3-trifluoropropene according to claim 1, further comprising the step of distilling the (E)-1-chloro-3,3,3-trifluoropropene composition after step (b).

5. The production process of (E)-1-chloro-3,3,3-trifluoropropene according to claim 1, wherein the amount of the hydrogen fluoride contained in the (E)-1-chloro-3,3,3-trifluoropropene composition before step (b) is 0.0001 to 10 parts by mass per 100 parts by mass of the (E)-1-chloro-3,3,3-trifluoropropene composition.

6. The production process of (E)-1-chloro-3,3,3-trifluoropropene according to claim 1, wherein the amount of the weak base used is 1 to 10 mol per 1 mol of the hydrogen fluoride contained in the (E) 1-chloro-3,3,3-trifluoropropene composition.

7. The production process of (E)-1-chloro-3,3,3-trifluoropropene according to claim 1,
   wherein the weak base is selected from the group consisting of carbonates, hydrocarbonates, phosphates, hydrogenphosphates, dihydrogenphosphates and $C_1$-$C_6$ carboxylates of alkali metals, and
   wherein the weak base is used in the form of a solution with water or an organic solvent.

8. The production process of (E)-1-chloro-3,3,3-trifluoropropene according to claim 1, wherein the weak base is a $C_3$-$C_{15}$ tertiary amine and is used in the form of a solution with water.

* * * * *